US011234980B2

(12) United States Patent
Csonka et al.

(10) Patent No.: US 11,234,980 B2
(45) Date of Patent: Feb. 1, 2022

(54) PHARMACEUTICAL COMPOSITION FOR THE TREATMENT OF PULMONARY ARTERIAL HYPERTENSION

(71) Applicant: Actelion Pharmaceuticals Ltd, Allschwil (CH)

(72) Inventors: Dénes Csonka, Allschwil (CH); Wassim Fares, Chapel Hill, NC (US); Hans Hoogkamer, Bubendorf (CH); Koen Torfs, Kasterlee (BE)

(73) Assignee: Actelion Pharmaceuticals Ltd, Allschwil (CH)

( * ) Notice: Subject to any disclaimer, the term of this patent is extended or adjusted under 35 U.S.C. 154(b) by 0 days.

(21) Appl. No.: 17/189,881

(22) Filed: Mar. 2, 2021

(65) Prior Publication Data

US 2021/0196715 A1 Jul. 1, 2021

Related U.S. Application Data

(63) Continuation of application No. PCT/EP2019/086754, filed on Dec. 20, 2019.

(30) Foreign Application Priority Data

| Dec. 21, 2018 | (WO) | PCT/EP2018/086724 |
| Jan. 25, 2019 | (WO) | PCT/EP2019/051830 |
| Apr. 18, 2019 | (WO) | PCT/EP2019/060151 |
| Jun. 21, 2019 | (WO) | PCT/EP2019/066494 |
| Jun. 27, 2019 | (WO) | PCT/EP2019/067186 |

(51) Int. Cl.
| *A61K 31/506* | (2006.01) |
| *A61P 9/12* | (2006.01) |
| *A61K 31/4965* | (2006.01) |
| *A61K 31/4985* | (2006.01) |

(52) U.S. Cl.
CPC ........ *A61K 31/506* (2013.01); *A61K 31/4965* (2013.01); *A61K 31/4985* (2013.01); *A61P 9/12* (2018.01)

(58) Field of Classification Search
CPC ................................ A61K 31/506; A61P 9/12
See application file for complete search history.

(56) References Cited

U.S. PATENT DOCUMENTS

| 7,094,781 | B2 | 8/2006 | Bolli et al. | |
| 8,268,847 | B2 * | 9/2012 | Clozel | A61P 9/10 |
| 8,367,685 | B2 * | 2/2013 | Adesuyi | A61K 9/2077 514/275 |
| 8,809,334 | B2 * | 8/2014 | Clozel | A61K 45/06 514/252.1 |
| 9,173,881 | B2 | 11/2015 | Clozel | |
| 9,265,762 | B2 | 2/2016 | Adesuyi et al. | |
| 9,597,331 | B2 | 3/2017 | Clozel | |
| 10,117,870 | B2 | 11/2018 | Adesuyi et al. | |
| 10,946,015 | B2 | 3/2021 | Lithgow et al. | |

FOREIGN PATENT DOCUMENTS

| WO | 2002/053557 | | 7/2002 |
| WO | 2007/031933 | A2 | 3/2007 |
| WO | 2008/026156 | A2 | 3/2008 |
| WO | 2010/018549 | A2 | 2/2010 |
| WO | 2018/089804 | A1 | 5/2018 |
| WO | 2018/153513 | A1 | 8/2018 |
| WO | 2020/152308 | A1 | 7/2020 |
| WO | 2020/201479 | A1 | 10/2020 |

OTHER PUBLICATIONS

Sidharta et al. The Journal of Clinical Pharmacology, 2013, vol. 53, No. 11, pp. 1131-1138 (Year: 2013).*
Monaco et al. Drug Design, Development and Therapy, May 18, 2016, vol. 10, pp. 1675-1682 (Year: 2016).*
OPSUMIT® (macitentan) Product Label (2013) (Accessed from https://www.accessdata.fda.gov/drugsatfda_docs/label/2013/204410s000lbl.pdf on Apr. 16, 2021) (Year: 2013).*
Sidharta et al. Eur. J. Clin. Pharmacol., 2011, vol. 67, pp. 977-984 (Year: 2011).*
Keating (Am J. Cardiovasc. Drugs, 2016, vol. 16, pp. 453-460) (Year: 2016).*
Mehta et al. Chest, 2017, vol. 151, No. 1, pp. 106-118 (Year: 2017).*
Jansa et al. Am. J. Cardiovasc. Drugs, 2018, vol. 18, pp. 1-11 (Year: 2018).*
Bedan et al. Basic & Clinical Pharmacology & Toxicology, 2018, vol. 123, pp. 103-113 (Year: 2018).*
Ahn et al: "Pharmacokinetic-Pharmacodynamic Relationships of Macitentan, a New Endothelin Receptor Antagonist, After Multiple Dosing in Healthy Korean Subjects", American Journal of Cardiovascular Drugs, vol. 14, No. 5, Oct. 2014 , pp. 377-385.
Anonymous: "Opsumit 10 mg film-coated tablets", EMA, Package leaflet: information for the user, Jan. 13, 2017, pp. 1-6, XP055679353, Retrieved from the Internet: URL:https://www.actelion.com/documents/enrebranded/our-products/opsumit-pil.pdf [retrieved on Mar. 24, 2020].

(Continued)

*Primary Examiner* — James D. Anderson
(74) *Attorney, Agent, or Firm* — BakerHostetler

(57) ABSTRACT

The present invention relates to high doses of macitentan, i.e. propylsulfamic acid [5-(4-bromo-phenyl)-6-[2-(5-bromo-pyrimidin-2-yloxy)-ethoxy]-pyrimidin-4-yl]-amide or pharmaceutically acceptable salts, solvates, hydrates or morphological forms thereof, or of aprocitentan, for use in the treatment and/or prevention of pulmonary arterial hypertension (PAH). Moreover, the present invention relates to the use of high doses of macitentan, or of aprocitentan, for the manufacture of a medicament for the treatment and/or prevention of PAH, as well as to a method for the treatment and/or prevention of PAH comprising high doses of macitentan or of aprocitentan. Further, the present invention relates to a dosage regimen for the treatment and/or prevention of PAH as well as to a combination of macitentan, or of aprocitentan, with one or more phosphodiesterase type 5 (PDE5) inhibitors, prostacyclin analogues, prostacyclin receptor agonists or soluble guanylate cyclase stimulators. Therein, PAH is preferably mild or moderate PAH. Moreover, the present invention relates to a pharmaceutical composition for the treatment of PAH comprising a high dose of macitentan or of aprocitentan.

30 Claims, 1 Drawing Sheet

(56) References Cited

OTHER PUBLICATIONS

Benza et al., "An evaluation of long-term survival from time of diagnosis in pulmonary arterial hypertension from the REVEAL Registry", Chest, 2012, 142(2), 448-456.

Benza et al., "The REVEAL Registry Risk Score Calculator in Patients Newly Diagnosed With Pulmonary Arterial Hypertension", Chest, 2012, 141(2), 354-362.

Bruderer et al., "Absorption, distribution, metabolism, and excretion of macitentan, a dual endothelin receptor antagonist, in humans", Xenobiotica, 2012, 42(9), 901-910.

European Medicines Agency, European Public Assessment Report for Opsumit, Procedure No. EMEA/H/C/002697/0000 (2013) at 20 "EMA Assessment Report".

Galie et al., "ESC/ERS Guidelines", European Heart Journal, 2016, 37, 67-119.

Graham et al., "2017 ERS/ATS standards for single-breath carbon monoxide uptake in the lung", Eur. Respir. J., 2017, 49, 31 pages.

Hullin, "New compounds for the treatment of pulmonary hypertension", Cardiovascular Medicine, 2018, 21(7-8), 195-199.

Iglarz et al., "Comparison of Pharmacological Activity of Macitentan and Bosentan in Preclinical Models of Systemic and Pulmonary Hypertension", Life Sci., 2014, 118, 333-339.

Iglarz et al., "Pharmacology of macitentan, an orally active tissue-targeting dual endothelin receptor antagonist", J. Pharmacol. Exp. Ther., 2008, 327(3), 736-745.

Kholdani, et al.,"Macitentan for the treatment of pulmonary arterial hypertension", Vascular Health and Risk Management, vol. 10, Nov. 25, 2014, pp. 665-673.

Kunita-Takanezawa et al., "Novel Dual Endothelin Receptor Antagonist Macitentan Reverses Severe Pulmonary Arterial Hypertension in Rats", J. Cardiovasc. Pharmacol., 2014, 64(5), 473-480.

Morrell et al., "Genetics and genomics of pulmonary arterial hypertension", Eur. Respir. J., Jan. 2019, 53(1): 1801899.

Simonneau et al., "Haemodynamic definitions and updated clinical classification of pulmonary hypertension", Eur. Respir. J., Jan. 2019, 53(1):1801913.

Yokoyama et al., "Tolerability, Safety, Pharmacokinetics, and Pharmacodynamics of Macitentan, a New Endothelin Receptor Antagonist, in Healthy Japanese Male Subjects", Rinsho Yakuri/Japanese Journal of Clinical Pharmacology and Therapeutics, 2016, 47, 143-150.

Adesuyi et al., U.S. Appl. No. 17/116,983, entitled "Stable Pharmaceutical Compositions Comprising a Pyrimidine-Sulfamide", filed Dec. 9, 2020.

Clozel, U.S. Appl. No. 17/185,238, entitled "Therapeutic Compositions", filed Feb. 25, 2021.

\* cited by examiner

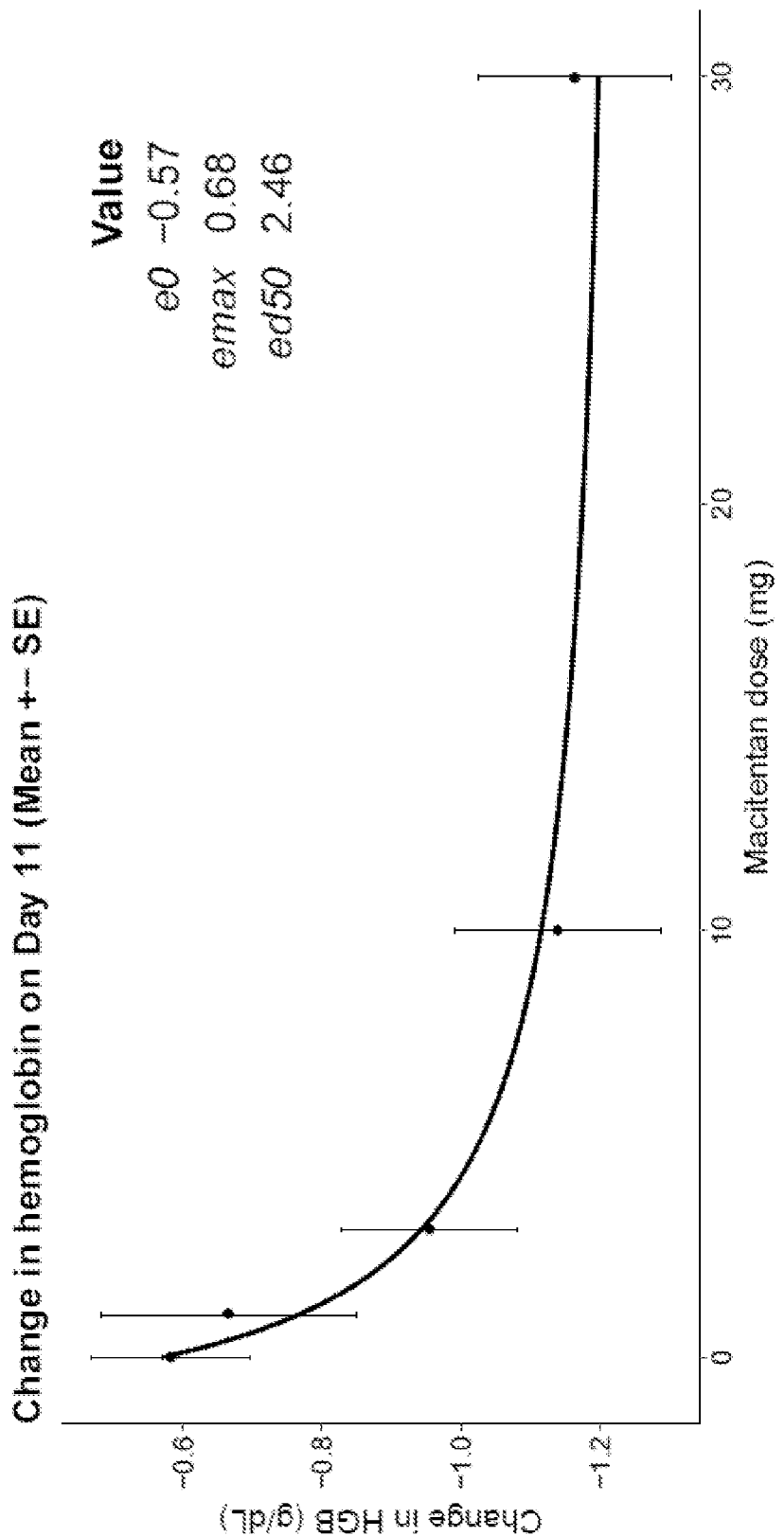

PHARMACEUTICAL COMPOSITION FOR THE TREATMENT OF PULMONARY ARTERIAL HYPERTENSION

CROSS-REFERENCE TO RELATED APPLICATIONS

This application is a continuation of International Patent Application No. PCT/EP2019/086754, filed Dec. 20, 2019, which claims priority to International Patent Application No. PCT/EP2018/086724, filed Dec. 21, 2018, International Patent Application No. PCT/EP2019/051830, filed Jan. 25, 2019, International Patent Application No. PCT/EP2019/060151, filed Apr. 18, 2019, International Patent Application No. PCT/EP2019/066494, filed Jun. 21, 2019, and International Patent Application No. PCT/EP2019/067186, filed Jun. 27, 2019, all disclosures of which are incorporated herein by reference in their entireties.

FIELD OF THE INVENTION

The present invention relates to high doses of macitentan (INN), i.e. propylsulfamic acid [5-(4-bromo-phenyl)-6-[2-(5-bromo-pyrimidin-2-yloxy)-ethoxy]-pyrimidin-4-yl]-amide or pharmaceutically acceptable salts, solvates, hydrates or morphological forms thereof for use in the treatment and/or prevention of pulmonary arterial hypertension (PAH). Moreover, the present invention relates to the use of high doses of macitentan for the manufacture of a medicament for the treatment and/or prevention of PAH, as well as to a method for the treatment and/or prevention of PAH comprising administering high doses of macitentan to a patient. Further, the present invention relates to a dosage regimen for the treatment and/or prevention of PAH as well as to a combination of macitentan with one or more phosphodiesterase type 5 (PDE5) inhibitors, prostacyclin analogues, prostacyclin receptor agonists or soluble guanylate cyclase stimulators. Therein, PAH is preferably mild or moderate PAH. Moreover, the present invention relates to a pharmaceutical composition for the treatment of PAH comprising a high dose of macitentan.

BACKGROUND

Pulmonary hypertension (PH) was reported for the first time in 1891 when the autopsy of a patient with sudden death revealed right ventricular hypertrophy and pulmonary artery sclerosis without any apparent cause. Pulmonary arterial hypertension (PAH) is a subgroup of PH and it is a progressive disease with elevated pulmonary vascular resistance (PVR) as the basic cause for increased right ventricular afterload and hypertrophy, which eventually proceeds to right ventricular dilatation and failure, and premature death. PH is clinically classified into five groups according to the World Health Organization (WHO) classification: pulmonary arterial hypertension (PAH) (group 1), PH related to left heart disease (group 2), PH due to lung disease and/or hypoxia (group 3), chronic thromboembolic PH and other pulmonary artery obstructions (group 4), and PH with unclear and/or multifactorial mechanisms (group 5) (Roger Hullin, Cardiovascular Medicine (2018), 21(7-8):195-199; Simonneau et al., Haemodynamic definitions and updated clinical classification of pulmonary hypertension. *Eur. Respir. J.* (2018), Dec. 13. pii: 1801913. doi: 10.1183/13993003.01913-2018. [Epub ahead of print]).

The present invention focuses on PAH which is haemodynamically characterised by the presence of a mean pulmonary artery pressure (PAP)>20 mm Hg, a pulmonary artery wedge pressure (PAWP)≤15 mm Hg and a PVR of equal to or more than (>) 3 Wood units, alternatively >2 Wood units, all measured at rest.

In particular, the present invention focuses on PAH which is haemodynamically characterised by the presence of a mean pulmonary artery pressure (PAP)≥25 mm Hg, a pulmonary artery wedge pressure (PAWP)≤15 mm Hg and a PVR of equal to or more than (>) 3 Wood units, alternatively >2 Wood units, all measured at rest.

The pathophysiology of PAH is characterised by an imbalance between molecules mediating vasoconstriction (e.g., endothelin or thromboxane) and/or molecules mediating vasodilation (e.g., prostacyclin and nitric oxide). Furthermore, mitogenic effects of these molecules, with specific pathomorphological changes in the pulmonary circulation are involved in disease progression.

Currently available compounds approved for specific treatment of PAH are in three different groups: a) endothelin receptor antagonists, b) phosphodiesterase type 5 inhibitors (PDE5 is) and soluble guanylate cyclase stimulators, and c) molecules interfering with the prostacyclin pathway. Treatment with these compounds in combination with general measures has increased 3-year survival after first diagnosis of idiopathic PAH from 48% in the 1980s to 74% in the last two decades, as shown in the REVEAL registry (Benza et al., An evaluation of long-term survival from time of diagnosis in pulmonary arterial hypertension from the REVEAL Registry. *CHEST* (2012), 142(2), 448-456; and *CHEST* (2012), 141(2):354-362).

SUMMARY OF THE INVENTION

It is an object of the present invention to provide a medication and/or treatment regimen for pulmonary arterial hypertension (PAH). In particular it is an object of the present invention to provide a medication and/or treatment regimen for the treatment of mild or moderate PAH. It is a further object of the present invention to provide a combination medication and/or treatment for PAH.

BRIEF DESCRIPTION OF THE FIGURES

FIG. 1 is a dose-response curve showing the change in hemoglobin (HGB) in function of the dose of macitentan administered to a human.

DETAILED DESCRIPTION

The present inventors have recognized that, despite fears of clinically relevant hemoglobin decreases, blood pressure decreases and/or edema or fluid retention increases, it is possible and safe and effective to treat PAH patients with high doses of macitentan. In particular, it is possible to decrease the progress of the disease, or even to improve the status of the disease.

In the present invention, macitentan is defined as propylsulfamic acid [5-(4-bromo-phenyl)-6-[2-(5-bromo-pyrimidin-2-yloxy)-ethoxy]-pyrimidin-4-yl]-amide, i.e. a compound of formula (I)

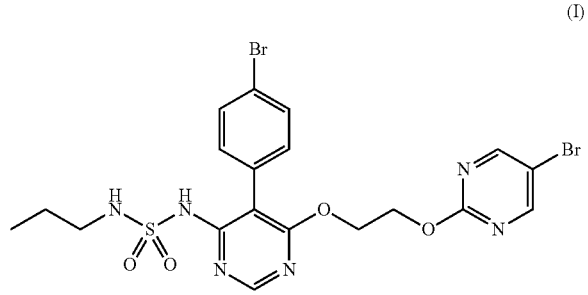 [SMILES: CCCNS(=O)(=O)Nc1ncnc(OCCOc2ncc(Br)cn2)c1-c1ccc(Br)cc1]

(I)

or a pharmaceutically acceptable salt, solvate, hydrate or morphological form thereof.

Macitentan is an endothelin receptor antagonist (ERA) that acts as an antagonist of two endothelin (ET) receptor subtypes, $ET_A$ and $ET_B$ (Kholdani et al, Macitentan for the treatment of pulmonary arterial hypertension. *Vasc. Health Risk Manag.* (2014), 10, 665-673). Its half-life in humans is about 16 hours and steady state is reached by the third day of administration (Bruderer et al., Absorption, distribution, metabolism, and excretion of macitentan, a dual endothelin receptor antagonist, in humans. *Xenobiotica* (2012), 42(9), 901-910). It is absorbed slowly into the plasma (Sidharta et al., Macitentan: entry-into-humans study with a new endothelin receptor antagonist. *Eur. J. Clin. Pharmacol.* (2011), 67, 977-984). Macitentan dealkylates into the active metabolite ACT-132577, which reaches its peak plasma concentration about 30 hours after the first dose is administered, and it has a half-life of approximately 48 hours. Although ACT-132577 has a lower affinity for the ET receptors than its parent compound (Iglarz et al., Pharmacology of macitentan, an orally active tissue-targeting dual endothelin receptor antagonist. *J. Pharmacol. Exp. Ther.* (2008), 327(3), 736-745), it maintains higher plasma concentrations than macitentan. Both compounds can be excreted from the body through the urine or feces.

It has previously been reported that the maximal or near-maximal effect of macitentan in rats is 10 mg/kg. (European Medicines Agency, European Public Assessment Report for Opsumit, Procedure No. EMEA/H/C/002697/0000 (2013) at 20 ("EMA Assessment Report")). It has also previously been reported that the maximal effective dose of macitentan in rats is 30 mg/kg (Id.; e.g., Iglarz et al., Comparison of Pharmacological Activity of Macitentan and Bosentan in Preclinical Models of Systemic and Pulmonary Hypertension. *Life Sci.* (2014), 118, 333-339; see also Kunita-Takanezawa et al., Novel Dual Endothelin Receptor Antagonist Macitentan Reverses Severe Pulmonary Arterial Hypertension in Rats. *J. Cardiovasc. Pharmacol.* (2014), 64(5), 473-480).

In a multiple-ascending dose study evaluating 1 mg, 3 mg, 10 mg, and 30 mg dosages of macitentan in healthy human subjects, plasma ET-1 concentrations at steady-state showed a dose-dependent increase, with no further increase beyond the 10 mg oral dose, indicating blockade at this dosage. (Id. at 40). The evaluators concluded that the 10 mg dose appeared to be close to the plateau of the pharmacological effect. (Id. at 48). The European Medicines Agency and the U.S. Food and Drug Administration have approved the 10 mg daily oral dosage of macitentan for the treatment of patients with pulmonary arterial hypertension. (EMA, Summary of Product Characteristics for Opsumit (Oct. 29, 2019) at 2; FDA, Prescribing Information for Opsumit (April 2019) at 1).

In the following, several aspects of the invention will be explained.

One aspect of the present invention relates to macitentan for use in the treatment and/or prevention of pulmonary arterial hypertension (PAH) in human, wherein the dosage of macitentan is more than 20 mg per day to equal to or less than 300 mg per day, for example, more than 20 mg per day to less than 250 mg per day. Preferably, the dosage is 25 mg to 200 mg.

According to a more preferred aspect, these dosages are applied once a day.

In the present invention, PAH is defined as pulmonary arterial hypertension in human.

The present invention focuses on PAH which is haemodynamically characterised by the presence of a mean pulmonary artery pressure (PAP)>20 mm Hg, a pulmonary artery wedge pressure (PAWP) 15 mm Hg and a PVR of equal to or more than (>) 3 Wood units, alternatively >2 Wood units, all measured at rest. In addition to the above hemodynamic characterization, PAH is characterized clinically by the absence of overt left-sided heart disease, severe lung disease, or known chronic thromboembolic disease.

In particular, the invention's focus is on PAH is characterized hemodynamically by a right heart catheterization as:
Mean pulmonary artery pressure (mPAP)≥25 mm Hg
Pulmonary occlusion wedge pressure (PAWP)≤15 mm Hg
Pulmonary vascular resistance equal to or more than (>) 3 Wood Units, alternatively >2 Wood units.

In addition to the above hemodynamic characterization, PAH is characterized clinically by the absence of overt left-sided heart disease, severe lung disease, or known chronic thromboembolic disease.

As described above-macitentan is currently administered as 10 mg oral dose once a day. However, with the present invention it is suggested to administer a high dosage of macitentan in order to improve the disease status, prevent the occurrence of disease worsening, improve or stabilize the WHO functional class and improve long-term survival and/or decrease hospitalization rate. Advantageously, if for instance compared to bosentan, there are fewer to no side effects on liver function and no or insignificant hepatotoxicity.

Further advantages are no further clinically relevant decrease in hemoglobin, no further clinically relevant decrease in blood pressure and/or no further clinically relevant increase in edema/fluid retention.

Another aspect of the present invention relates to macitentan for use in the treatment and/or prevention of pulmonary arterial hypertension (PAH) according to aspect (a), wherein the PAH is mild or moderate PAH, preferably moderate PAH.

Surprisingly it has been found that in mild and moderate PAH, the disease status could be improved or stabilized; in particular, the WHO functional class could be improved in mild and moderate patients. Functional capacity, as measured with a 6-minute walk test, could also be improved.

The term "mild PAH" approximately equates to WHO Functional Class I and II.

The term "moderate PAH" approximately equates to WHO Functional Class III.

In contrast thereto, WHO Functional Class IV equates to severe PAH.

The WHO Functional Classes (WHO FC) are commonly known and defined as follows:

WHO FC I: No symptoms of pulmonary arterial hypertension with exercise or at rest. It is rare for a patient to be diagnosed while still a class I. Patients that are being screened because of high risk factors for developing PAH, such as patients with scleroderma or family history of PAH, may rarely be diagnosed as class I. More often this classification is used to describe patients who have demonstrated a substantial response to therapy who were once a class II or III but have improved to a class I.

WHO FC II: No symptoms at rest but uncomfortable, fatigued, or short of breath with normal activity such as climbing a flight of stairs, grocery shopping, or making the bed.

WHO FC III: Patients may not have symptoms at rest but normal activities are greatly limited by shortness of breath, fatigue, or near fainting. Patients in this class have a difficult time doing normal chores around the house and have to take breaks while doing activities of daily living.

WHO FC IV: Symptoms at rest or severe symptoms with any activity.

Patients in this class may faint with activity or while bending over with their heads lowered. Many patients in this class are also volume overloaded with edema in their feet and ankles from right heart failure.

A more detailed assessment for mild PAH is determined as follows: (dmild): Fulfilling at least 3 of the following criteria:
WHO FC I or II;
Six-minute walk distance (6MWD)>440 m;
B-type natriuretic peptide (BNP)<50 ng/L or N-terminal pro-B-type natriuretic peptide (NT-proBNP)<300 ng/L; or RAP<8 mmg HG;
CI≥2.5 L/min/m$^2$ or SvO$_2$>65%;
and not fulfilling any of the (dsevere) criteria.

A more detailed assessment for severe PAH is determined as follows: (dsevere): Fulfilling at least two of the following features, including CI or SvO$_2$:
WHO FC IV;
6MWD<165 meters;
BNP>300 ng/L or NT-proBNP >1400 ng/L; or RAP>14 mmg HG
CI<2.0 L/min/m$^2$ or SvO$_2$<60%.

A more detailed assessment for moderate PAH is determined as follows: (dmoderate) the aforementioned assessments of the (dmild) criteria and the (dsevere) criteria do neither allow to classify the patient's PAH as mild PAH nor allow to classify the patient's PAH as severe PAH.

Preferably, the concentration of NT-proBNP, rather than the concentration of BNP, will be determined and used to decide whether the patient has mild, moderate or severe PAH according to the preceding more detailed assessment definitions.

BNP is measured as follows: a plasma sample is collected and shipped frozen (−20° C. or below) in a plastic EDTA tube and analyzed with an immunochemiluminometric assay (ICMA). The principles of this ICMA assay are as follows:
A commercially available kit (Triage® BNP test) with the following 3 working solutions/suspensions is used:
S1a: paramagnetic particles coated with mouse omniclonal anti-human BNP antibody suspended in TRIS buffered saline solution (150 mM NaCl, 50 mM Tris-HCl, pH 7.6 aq. solution), with bovine serum albumin (BSA), 0.1% ProClin™ 300 (0.60-1.00% 2-methyl-4-isothiazolin-3-one and 2.10-2.80% 5-chloro-2-methyl-4-isothiazolin-3-one aq. solution) and <0.1% sodium azide;
S1 b: purified mouse and goat IgG in Tris buffered saline solution (150 mM NaCl, 50 mM Tris-HCl, pH 7.6 aq. solution), with bovine serum albumin (BSA), 0.1% ProClin™ 300 (0.60-1.00% 2-methyl-4-isothiazolin-3-one and 2.10-2.80% 5-chloro-2-methyl-4-isothiazolin-3-one aq. solution) and <0.1% sodium azide; and
S1c: mouse monoclonal anti-human BNP antibody-alkaline phosphatase bovine conjugate in PBS buffered saline solution (pH 7.4; 137 mmol/L NaCl, 2.7 mmol/L KCl, 10 mmol/L Na$_2$HPO$_4$ and 1.8 mmol/L KH$_2$PO$_4$), with bovine serum albumin (BSA), 0.1% ProClin™ 300 (0.60-1.00% 2-methyl-4-isothiazolin-3-one and 2.10-2.80% 5-chloro-2-methyl-4-isothiazolin-3-one aq. solution) and <0.1% sodium azide.

The blood sample (500 µL) is collected from the patient and placed in a plastic blood draw tube containing K$_2$EDTA as an anticoagulant. The blood sample should be mixed by gently inverting the tube several times.

The suspension S1a and the solution S1c are placed in a reaction vessel and 55 µL of the blood sample is added thereto.

After incubation in the reaction vessel, a magnetic field is used to hold the materials bound to the solid phase and unbound materials are washed away using the solution S1 b.

A chemiluminescent substrate, Lumi-Phos® 530 (Chemical Abstracts Substance No. 146239-76-1), is then added into the reaction vessel and light generated by the reaction is measured by a luminometer. The resulting light is proportional to the BNP concentration, thus allowing to determine the BNP concentration in the sample.

To ensure accuracy of the ICMA assay results, the luminometer should regularly be calibrated with commercially available reference solutions.

NT-proBNP is measured as follows: a serum or plasma sample is collected and shipped at ambient temperature if within 3 days of collection or frozen in a red-top tube, after centrifugation, and analyzed with an electrochemiluminescence immunoassay (ECLIA). The principles of this ECLIA assay are as follows:
A commercially available kit with the following 3 working solutions/suspensions is used:
S1: A suspension (6.5 mL) of streptavidin-coated microparticles (0.72 mg/mL) containing preservative;
S2: A solution (9 mL) of Anti-NT-proBNP-Ab-biotin, containing Biotinylated monoclonal anti-NT-proBNP antibody (mouse) (1.1 µg/mL), phosphate buffer 40 mmol/L, pH 5.8 and preservative; and
S3: A solution (9 mL) of Anti-NT-proBNP-Ab-Ru (bpy), containing a monoclonal NT-proBNP-specific antibody labeled with the tris(2,2'-bipyridyl)ruthenium(II) complex (Ru(bpy)) (1.1 µg/mL), phosphate buffer 40 mmol/L, pH 5.8 and preservative.

The sample (15 µL) is first incubated with the solutions S2 and S3; the biotinylated monoclonal NT-proBNP-specific antibody and the monoclonal NT-proBNP-specific antibody labeled with a ruthenium complex form a sandwich complex.

A second incubation is then performed, whereby, after addition of the suspension S1, the complex becomes bound to the solid phase via interaction of biotin and streptavidin.

The reaction mixture is aspirated into the measuring cell where the microparticles are magnetically captured onto the surface of the electrode. Unbound substances are then removed. Application of a voltage to the electrode then induces chemiluminescent emission which is measured by a photomultiplier.

Results are determined based on a calibration curve using commercially available reference solutions.

CI is measured as follows: CI reflects the flow of blood (liters/minute) through the heart, which is called cardiac output (CO), standardized to the patient's body surface area (BSA); the CI is thus expressed in liters/minute/meter$^2$. A right heart catheterization (RHC) is a standard procedure used to diagnose PAH. It is an invasive procedure during which a catheter is inserted through a large vein and then the catheter is advanced to the right side of the heart and then into the pulmonary artery. There are different methods to measure the CI, but the most common methods are Fick cardiac index method or Thermodilution cardiac index method. These are standardized and well-established methods. The most accepted method is the thermodilution method. According to this invention, the thermodilution (TD) method will be the specific method used to measure CI. TD determines the CO based on how fast a set amount of fluids (typically at room temperature, i.e., 25° C.) moves from the right atrium [injected into the proximal port of the pulmonary artery (PA) catheter] to the PA (detected by a thermo-sensor close to the tip of the distal part of the PA catheter). An area under the curve (AUC) of the change in temperature is generated. This is to be repeated at least 3 times, and then the average value will be calculated, but the values should be within (+/−) 10-15% of each other for these measurements to be valid. The curves should also be assessed to make sure the flow is smooth without sharp changes in the curve that may suggest erroneous injections or measurements. Based on the average AUC obtained and the patient's BSA, defined as follows $$BSA=\sqrt{[(\text{height in cm} \times \text{weight in kg})/3600]}$$

the CI is calculated.

RAP is measured as follows: the RAP (occasionally referred to as mRAP, i.e. mean RAP) is also measured during the RHC procedure as outlined above for measuring the CI. There is a pressure sensor at the tip of the catheter that is inserted in a vein that makes its way into the right side of the heart. The sensor measures the pressure when the catheter tip is in the right atrium, and that measured pressure is the RAP. It is a single measurement.

$SvO_2$ is measured as follows: the $SvO_2$ is also measured during the RHC procedure as outlined above for measuring the CI. When the catheter tip is in a central vein or the right atrium, blood is withdrawn and the oxygen 'concentration'/'content' (partial pressure of oxygen in the blood) in that blood sample is analyzed using standard blood gas analyzers/sensors; the % of oxygenation in that blood sample is the $SvO_2$. It is also a single measurement.

For more detailed assessment, mild and moderate PAH can be defined according to an algorithm which is based on the Registry to Evaluate Early and Long-term PAH Diseases Management (REVEAL Registry). The algorithm may be described as comprising the following steps:

(i) Determination of the WHO Group I Subgroup of the patient and assigning
  +1 score for APAH-CTD (PAH associated with connective tissue disease),
  +2 scores for APAH-PoPH (PAH associated with portopulmonary hypertension),
  +2 scores for FPAH (familial PAH, which is currently referred to heritable PAH);
  0 score for any other subgroups of PAH;
(ii) Determination of demographics and comorbidities and assigning
  +1 score for renal insufficiency,
  +2 scores for male age >60 years,
  0 score for other patients;
(iii) Determination of the WHO Functional Class and assigning
  −2 scores for WHO FC I
  0 scores for WHO FC II
  +1 score for WHO FG III
  +2 scores for WHO FG IV
(iv) Determination of vital signs and assigning
  +1 score for SBP (systolic systemic blood pressure) <110 mmHg,
  +1 score for HR (heart rate) >92 BPM (beats per minute),
  0 score for any other cases;
(v) Determination of the 6-minute walk distance and assigning
  −1 score for ≥440 meters,
  +1 score for <165 meters,
  0 scores for any other cases;
(vi) Determination of BNP (brain natriuretic peptide) and assigning
  −2 scores for BNP<50 pg/mL,
  +1 score for BNP>180 pg/mL,
  0 score for BNP from 50 pg/mL to 180 pg/mL;
(vii) Determination of an echocardiogram and assigning
  +1 score for pericardial effusion,
  0 scores for any other cases;
(viii) Pulmonary function test and assigning
  −1 score for % predicted DLCO≥80% (diffusing capacity of lung for Carbon monoxide),
  +1 score for % predicted DLCO≤32%,
  0 scores for % predicted DLCO between 32% and 80%;
(ix) Right heart catherization and assigning
  +1 score for RAP (mean right arterial pressure)>20 mm Hg within 1 year,
  +2 scores for PVR (pulmonary vascular resistance)>32 Wood units,
  0 scores for any other cases;
(x) Summarize the scores obtained in steps (i) to (ix) and add the number 6;
(xi) mild PAH is assigned for a score from 1 to 7, and moderate PAH is assigned for a score of 8 or 9.

In the above algorithm "+" means to add, "−" means to subtract.

A Wood Unit is the measure of a simplified system for measuring pulmonary vascular resistance (PVR) that uses increments of pressure. Measurement of PVR is made by subtracting pulmonary artery wedge pressure from the mean pulmonary arterial pressure and dividing by cardiac output in liters per minute.

Hence, mild PAH is associated with a score of 1-7, and moderate PAH is associated with a score of 8 or 9.

For further definitions, it is expressly pointed to the ESC/ERS Guidelines, *European Heart Journal* (2016), 37, 67-119.

Hereditary transmission of PAH has been reported in approximately 6% to 10% of patients with PAH; in 50% to 90% of these individuals, mutations in BMPR2 (bone morphogenetic protein receptor type-2) have been identified. The mutations in BMPR2 in familial pulmonary arterial hypertension (FPAH) are characterized by genetic anticipation and incomplete penetrance. FPAH is also referred to as HPAH (hereditary PAH). The phenotype is not expressed in all generations, but when expressed, occurs at an earlier age and is associated with more severe and rapidly progressive disease. Many other genetic mutations have been identified to be associated with familial (heritable) PAH, but these are much less common than the BMPR2 mutation (Morrell et al., *Eur. Respir. J.* (2018), Dec. 13. pii: 1801899. doi: 10.1183/13993003.01899-2018. [Epub ahead of print]).

In the present invention, APAH-CTD (PAH associated with connective tissue disease) is characterized by PAH in someone who also has an autoimmune disease, also called connective tissue disease. The most common connective tissue diseases that are associated with PAH are scleroderma (systemic sclerosis), Lupus (systemic lupus erythematosus/SLE), mixed connective tissue diseases and Sjogren's disease.

In the present invention, APAH-PoPH (PAH associated with porto-pulmonary hypertension) is characterized by PAH that is associated with portal hypertension. Portal hypertension is defined as increased pressure in the portal vein as evidenced by an increase in the gradient of pressure between the portal vein and the hepatic vein by more than 5 mm Hg (it becomes clinically significant if the pressure gradient is 10 mm Hg). The portal vein carries blood from the gastrointestinal system to the liver. Although this happens more often in the presence of advanced liver disease causing the portal hypertension, porto-pulmonary hypertension may happen in the absence of liver disease as long as there is portal hypertension.

PAH associated with portal hypertension is commonly referred to as PoPH. This entity should not be confused with hepatopulmonary syndrome, which is characterized by abnormal pulmonary vasodilation and hypoxaemia. However, overlaps between both conditions may occur. As implied by the term, PoPH is associated with the presence of portal hypertension as defined above, not necessarily with the presence of liver disease. However, as cirrhotic liver disease is by far the most common cause of portal hypertension, PoPH is most frequently encountered in patients with cirrhosis.

A complete diagnostic workup including a right heart catheterization (RHC) is required to assess disease severity, haemodynamic profile and other potential causes of PH, including lung disease, LHD or chronic thromboembolic disease (ESC/ERS Guidelines, *European Heart Journal* (2016), 37, 67-119).

In the present invention, renal insufficiency is characterized by a glomerular filtration rate (GFR) below 90 ml/min/1.73 m². The GFR is obtained by obtaining standardized creatinine blood concentration (SCr) from the patient and using the MDRD equation which is as follows:

$$GFR=175 \times SCr^{-1.154} \times age^{-0.203} \times (0.742 \text{ if female}) \times (1.21 \text{ if black})$$

The GFR obtained according to the equation above is expressed in mL/min per 1.73 m² body surface area. If the body surface area of the patient is different from 1.73 m², the value obtained for the GFR through the MDRD equation above should be converted accordingly.

Pericardial effusion is a collection of fluid around the heart. Normally, there should be a very thin, typically invisible to the normal eye, layer of fluid that acts as lubricant to prevent friction between the heart and the pericardium (fibrinous layer surrounding and protecting the heart). In the setting of advanced PH (as well as many other diseases), that fluid builds up and forms a collection around the heart, defined as pericardial effusion. The presence of such an effusion portends poor prognosis as it signifies advanced PH and right heart dysfunction/failure.

DLCO is measured via pulmonary function tests. These tests are performed as described in Graham et al., 2017 ERS/ATS standards for single-breath carbon monoxide uptake in the lung, *Eur. Respir. J.* (2017), 49, 1600016.

RHC is an invasive, typically, outpatient procedure that involves inserting a catheter through a central vein and then passing it through the right sided heart chambers to reach the pulmonary artery. Different measurements are taken during this procedure including pressures and blood flow termed cardiac output.

Another aspect of the present invention relates to macitentan for use in the treatment and/or prevention of PAH according to aspect (a) or (b), wherein the dosage of macitentan is 60 to 90 mg per day. Preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. Further preferred ranges are 72 to 78 mg per day. According to a more preferred aspect, these dosages are applied once a day.

In a preferred aspect, these dosages relate to macitentan for use in the treatment and/or prevention of mild or moderate PAH, preferably moderate PAH.

A further aspect of the present invention relates to macitentan for use in the treatment and/or prevention of PAH according to aspect (a) or (b), wherein the dosage of macitentan is 25 to 50 mg per day. Preferably, the dosage is 30 to 45 mg per day, more preferably 35 to 40 mg per day and most preferably 37.5 mg per day. It is to be understood that each of the lower limits disclosed above may be combined with each of the upper limits, i.e. the dosage could also be from 25 to 45 mg per day, or from 25 to 40 mg per day. Also disclosed are doses from 30 to 50 mg, or 30 to 40 mg per day. Further preferred ranges are 36 to 39 mg per day. According to a more preferred aspect, these dosages are applied once a day.

In a preferred aspect, these dosages relate to macitentan for use in the treatment and/or prevention of mild or moderate PAH, preferably moderate PAH.

A further aspect of the present invention relates to macitentan for use in the treatment and/or prevention of PAH according to aspect (a) or (b), wherein the dosage of macitentan is 110 to 200 mg per day. Preferably, the dosage is 125 to 175 mg per day, more preferably 140 to 160 mg per day and most preferably 150 mg per day. It is to be understood that each of the lower limits disclosed above may be combined with each of the upper limits, i.e. the dosage could also be from 110 to 175 mg per day, from 110 to 160 mg per day or from 110 to 150 mg per day. Also disclosed are doses from 125 to 160 mg or 140 to 175 mg per day. Further preferred ranges are 145 to 155 mg per day. According to a more preferred aspect, these dosages are applied once a day.

In a preferred aspect, these dosages relate to macitentan for use in the treatment and/or prevention of mild or moderate PAH, preferably moderate PAH.

A further aspect of the present invention relates to macitentan for use in the treatment and/or prevention of PAH according to aspect (a) or (b), wherein the dosage of macitentan is 60 to 90 mg twice per day. Preferably, the dosage is 65 to 85 mg twice per day, more preferably 70 to 80 mg twice per day and most preferably 75 mg twice per day. It is to be understood that each of the lower limits disclosed above may be combined with each of the upper limits, i.e. the dosage could also be from 60 to 85 mg twice per day, from 60 to 80 mg twice per day, or from 60 to 75 mg twice per day. Also disclosed are dosages from 65 to 90 mg twice per day, or 65 to 75 mg twice per day. Further preferred ranges are 72 to 78 mg twice per day.

In a preferred aspect, these dosages relate to macitentan for use in the treatment and/or prevention of mild or moderate PAH, preferably moderate PAH.

A further aspect of the present invention relates to macitentan for use in the treatment and/or prevention of PAH according to aspect (a) or (b), wherein the dosage of macitentan is 25 to 50 mg twice per day, preferably 30 to 45 mg twice per day, more preferably 35 to 40 mg twice per day and most preferably 37.5 mg twice per day. It is to be understood that each of the lower limits disclosed above may be combined with each of the upper limits, i.e. the dosage could also be from 25 to 45 mg twice per day, or from 25 to 40 mg twice per day. Also disclosed are doses from 30 to 50 mg twice per day, or 30 to 40 mg twice per day. Further preferred ranges are 36 to 39 mg twice per day.

In a preferred aspect, these dosages relate to macitentan for use in the treatment and/or prevention of mild or moderate PAH, preferably moderate PAH.

A further aspect of the present invention relates to macitentan for use in the treatment and/or prevention of PAH according to aspect (a) or (b), wherein the dosage of macitentan is escalated from 10 mg per day, followed by 25 to 50 mg per day, preferably 37.5 mg per day, and optionally followed by 60 to 90 mg per day, preferably 75 mg per day. Therein "followed by 25 to 50 mg per day" means preferably, the dosage is 30 to 45 mg per day, more preferably 35 to 40 mg per day and most preferably 37.5 mg per day. It is to be understood that each of the lower limits disclosed may be combined with each of the upper limits, i.e. the dosage could also be from 25 to 45 mg per day, or from 25 to 40 mg per day. Also disclosed are doses from 30 to 50 mg, or 30 to 40 mg per day. Further preferred ranges are 36 to 39 mg per day. It is to be understood that any escalation to a higher dose may be followed by return to the lower dose in case the higher dose is not tolerated.

Moreover, the phrase "optionally followed by 60 to 90 mg per day" means preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. Further preferred ranges are 72 to 78 mg per day. It is to be understood that any escalation to a higher dose may be followed by return to the lower dose in case the higher dose is not tolerated.

According to a more preferred aspect, these dosages are applied once a day.

At present, the dosage of macitentan for use in the treatment of PAH is 10 mg per day. Patients obtaining this dosage may receive an immediate dose escalation to 37.5 mg per day, optionally followed by 75 mg per day.

A further aspect of the present invention relates to macitentan for use in the treatment and/or prevention of PAH according to aspect (a) or (b), wherein the dosage of macitentan is escalated from 10 mg per day, followed by 25 to 50 mg per day, preferably 37.5 mg per day, optionally followed by 60 to 90 mg per day, preferably 75 mg per day, optionally followed by 110 to 200 mg per day, preferably 150 mg per day.

The phrase "optionally followed by 110 to 200 mg per day" means preferably, the dosage is 125 to 175 mg per day, more preferably 140 to 160 mg per day and most preferably 150 mg per day. It is to be understood that each of the lower limits disclosed above may be combined with each of the upper limits, i.e. the dosage could also be from 110 to 175 mg per day, from 110 to 160 mg per day or from 110 to 150 mg per day. Also disclosed are doses from 125 to 160 mg or 140 to 175 mg per day. Further preferred ranges are 145 to 155 mg per day. According to a more preferred aspect, these dosages are applied once a day.

In a preferred aspect, these dosages relate to macitentan for use in the treatment and/or prevention of mild or moderate PAH, preferably moderate PAH.

A further aspect of the present invention relates to macitentan for use in the treatment and/or prevention of PAH according to aspect (a) or (b), wherein the dosage of macitentan is escalated from 10 mg per day, followed by 60 to 90 mg per day, preferably 75 mg once per day or 37.5 mg twice a day.

The phrase "optionally followed by 60 to 90 mg per day" means preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. Further preferred ranges are 72 to 78 mg per day. It is to be understood that any escalation to a higher dose may be followed by return to the lower dose in case the higher dose is not tolerated.

According to a more preferred aspect, these dosages are applied once a day.

A further aspect of the present invention relates to macitentan for use in the treatment and/or prevention of PAH according to aspect (a) or (b), wherein the dosage of macitentan is escalated from 10 mg per day, followed by 60 to 90 mg per day, preferably 75 mg once per day or 37.5 mg twice a day, optionally followed by 110 to 200 mg per day, preferably 150 mg per day.

The phrase "optionally followed by 110 to 200 mg per day" means preferably, the dosage is 125 to 175 mg per day, more preferably 140 to 160 mg per day and most preferably 150 mg per day. It is to be understood that each of the lower limits disclosed above may be combined with each of the upper limits, i.e. the dosage could also be from 110 to 175 mg per day, from 110 to 160 mg per day or from 110 to 150 mg per day. Also disclosed are doses from 125 to 160 mg or 140 to 175 mg per day. Further preferred ranges are 145 to 155 mg per day. According to a more preferred aspect, these dosages are applied once a day.

At present, the dosage of macitentan for use in the treatment of PAH is 10 mg per day. Patients obtaining this dosage may receive an immediate dose escalation to 75 mg per day or to 150 mg per day.

In a preferred aspect, these dosages relate to macitentan for use in the treatment and/or prevention of mild or moderate PAH, preferably moderate PAH.

A further aspect of the present invention relates to macitentan for use in the treatment and/or prevention of PAH according to aspect (h), wherein the dosage of macitentan is escalated from 10 mg once per day, preferably for 15 to 45 days; followed by 25 to 50 mg per day, preferably 37.5 mg once per day, preferably for 15 to 45 days; and optionally followed by 60 to 90 mg per day, preferably by 75 mg once per day or 37.5 mg twice per day. It is to be understood that any escalation to a higher dose may be followed by return to the lower dose in case the higher dose is not tolerated.

Therein, the term "15 to 45 days" means preferably 20 to 40 days, more preferably 21 to 35 days, and most preferably 28 to 30 days, i.e. about one month.

Moreover, the phrase "followed by 25 to 50 mg per day" means preferably, the dosage is 30 to 45 mg per day, more preferably 35 to 40 mg per day and most preferably 37.5 mg per day. It is to be understood that each of the lower limits disclosed may be combined with each of the upper limits, i.e. the dosage could also be from 25 to 45 mg per day, or from 25 to 40 mg per day. Also disclosed are doses from 30 to 50 mg, or 30 to 40 mg per day. Further preferred ranges are 36 to 39 mg per day.

Moreover, the phrase "followed by 60 to 90 mg per day" means preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. Further preferred ranges are 72 to 78 mg per day, or 36 to 39 mg twice per day.

According to a more preferred aspect, these dosages are applied once a day.

A further aspect of the present invention relates to macitentan for use in the treatment and/or prevention of PAH according to aspect (h), wherein the dosage of macitentan is escalated from 10 mg once per day, preferably for 15 to 45 days; followed by 25 to 50 mg per day, preferably 37.5 mg once per day, preferably for 15 to 45 days; optionally followed by 60 to 90 mg per day, preferably by 75 mg once per day or 37.5 mg twice per day, preferably for 15 to 45 days; optionally followed by 110 to 200 mg per day, preferably 150 mg per day.

The phrase "optionally followed by 110 to 200 mg per day" means preferably, the dosage is 125 to 175 mg per day, more preferably 140 to 160 mg per day and most preferably 150 mg per day. It is to be understood that each of the lower limits disclosed above may be combined with each of the upper limits, i.e. the dosage could also be from 110 to 175 mg per day, from 110 to 160 mg per day or from 110 to 150 mg per day. Also disclosed are doses from 125 to 160 mg or 140 to 175 mg per day. Further preferred ranges are 145 to 155 mg per day. According to a more preferred aspect, these dosages are applied once a day.

In a preferred aspect, these dosages relate to macitentan for use in the treatment and/or prevention of mild or moderate PAH, preferably moderate PAH.

(k) A further aspect of the present invention relates to macitentan for use in the treatment and/or prevention of PAH according to aspect (i), wherein the dosage of macitentan is escalated from 10 mg once per day, preferably for 15 to 45 days; followed by 60 to 90 mg per day, preferably by 75 mg once per day or 37.5 mg twice per day.

Therein, the term "15 to 45 days" means preferably 20 to 40 days, more preferably 21 to 35 days, and most preferably 28 to 30 days, i.e. about one month.

The phrase "followed by 60 to 90 mg per day" means preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. Further preferred ranges are 72 to 78 mg per day, or 36 to 39 mg twice per day.

A further aspect of the present invention relates to macitentan for use in the treatment and/or prevention of PAH according to (i), wherein the dosage of macitentan is escalated from 10 mg once per day, preferably for 15 to 45 days; followed by 60 to 90 mg per day, preferably by 75 mg once per day or 37.5 mg twice per day, preferably for 15 to 45 days; optionally followed by 110 to 200 mg per day, preferably 150 mg per day. The phrase "optionally followed by 110 to 200 mg per day" means preferably, the dosage is 125 to 175 mg per day, more preferably 140 to 160 mg per day and most preferably 150 mg per day. It is to be understood that each of the lower limits disclosed above may be combined with each of the upper limits, i.e. the dosage could also be from 110 to 175 mg per day, from 110 to 160 mg per day or from 110 to 150 mg per day. Also disclosed are doses from 125 to 160 mg or 140 to 175 mg per day. Further preferred ranges are 145 to 155 mg per day.

According to a more preferred aspect, these dosages are applied once a day.

In a preferred aspect, these dosages relate to macitentan for use in the treatment and/or prevention of mild or moderate PAH, preferably moderate PAH.

(l) A further aspect of the present invention relates to macitentan for use in the treatment and/or prevention of PAH according to any one of aspects (a) to (d), wherein the dosage of macitentan is escalated to 25 to 50 mg per day, preferably 37.5 mg per day; preferably for 15 to 45 days; optionally followed by 60 to 90 mg per day, preferably by 75 mg per day; provided that the patient is already treated with an endothelin receptor antagonist preferably selected from bosentan and ambrisentan. It is to be understood that any escalation to a higher dose may be followed by return to the lower dose in case the higher dose is not tolerated.

Therein, the term "15 to 45 days" means preferably 20 to 40 days, more preferably 21 to 35 days, and most preferably 28 to 30 days, i.e. about one month.

Moreover, the phrase "followed by 25 to 50 mg per day" means preferably, the dosage is 30 to 45 mg per day, more preferably 35 to 40 mg per day and most preferably 37.5 mg per day. It is to be understood that each of the lower limits disclosed may be combined with each of the upper limits, i.e. the dosage could also be from 25 to 45 mg per day, or from 25 to 40 mg per day. Also disclosed are doses from 30 to 50 mg, or 30 to 40 mg per day. Further preferred ranges are 36 to 39 mg per day.

Moreover, the phrase "followed by 60 to 90 mg per day" means preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. Further preferred ranges are 72 to 78 mg per day, or 36 to 39 mg twice per day.

It is to be understood, that optionally, the dosage of macitentan can be further raised from 110 to 200 mg per day. The dosage is thereby escalated as in aspect (i), (j) or (k).

According to a more preferred aspect, these dosages are applied once a day.

In a preferred aspect, these dosages relate to macitentan for use in the treatment and/or prevention of mild or moderate PAH, preferably moderate PAH.

(m) A further aspect of the present invention relates to macitentan for use in the treatment and/or prevention of PAH according to any one of aspects (a) to (c), wherein the dosage of macitentan is 60 to 90 mg per day, preferably 75 mg per day; provided that the patient is already treated with an endothelin receptor antagonist preferably selected from bosentan, and ambrisentan.

The phrase "60 to 90 mg per day" means preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. Further preferred ranges are 72 to 78 mg per day, or 36 to 39 mg twice per day.

It is to be understood, that optionally, the dosage of macitentan can be further raised from 110 to 200 mg per day. The dosage is thereby escalated as in aspect (i), (j) or (k).

According to a more preferred aspect, these dosages are applied once a day.

In a preferred aspect, these dosages relate to macitentan for use in the treatment and/or prevention of mild or moderate PAH, preferably moderate PAH.

(n) A further aspect of the present invention relates to macitentan for use in the treatment and/or prevention of PAH according to any one of aspects (a) to (m), wherein macitentan is combined with a PDE5 inhibitor and/or a prostacyclin analogue, and/or a prostacyclin receptor agonist and/or a soluble guanylate cyclase stimulator.

Inhibition of the cyclic guanosine monophosphate (cGMP) degrading enzyme phosphodiesterase type 5 results in vasodilation through the NO/cGMP pathway at sites expressing this enzyme. Since the pulmonary vasculature contains substantial amounts of phosphodiesterase type 5, the potential clinical benefit of phosphodiesterase type 5 inhibitors (PDE5 is) has been investigated in PAH. In addition, PDE5 is exert antiproliferative effects (ESC/ERS Guidelines; *European Heart Journal* (2016), 37, 67-119).

Prostacyclin is produced predominantly by endothelial cells and induces potent vasodilation of all vascular beds. This compound is the most potent endogenous inhibitor of platelet aggregation and also appears to have both cytoprotective and antiproliferative activities. Dysregulation of the prostacyclin metabolic pathways has been shown in patients with PAH as assessed by a reduction of prostacyclin synthase expression in the pulmonary arteries and of prostacyclin urinary metabolites. The clinical use of prostacyclin in patients with PAH has been extended by the synthesis of stable analogues that possess different pharmacokinetic properties but share qualitatively similar pharmacodynamic effects (ESC/ERS Guidelines; *European Heart Journal* (2016), 37, 67-119).

No Drug-Drug Interaction has been observed for macitentan and its active metabolite, ACT-132577 so far.

For example, macitentan 10 mg per day o.d. has not shown any effect on the pharmacokinetics of 1 mg rosuvastatin, which suggests that BCRP transporters have not been inhibited. BCRP is an efflux pump located in the gut, liver canalicular membrane, and kidney, and is exposed to intracellular drug concentrations in the liver and the kidney.

Macitentan and ACT-132577 activated human PXR with $EC_{50}$ values of 1.1 to 1.2 µM and 7.2 to 8.7 µM, respectively. In human hepatocytes, both compounds elicited concentration-dependent increases in CYP3A4 mRNA and enzyme activity.

Predicted peak plasma concentrations of macitentan and ACT-132577 in PAH patients at 75 mg per day dose are expected to be around 5 µM and 14 µM, respectively, based on the PK Sub-study and assuming dose linearity. Taking into account the high degree of protein binding, free plasma concentrations are expected to be in the range of 0.02 µM to 0.07 µM for macitentan and ACT-132577, respectively. It is not likely that these unbound concentrations of macitentan and ACT-132577 result in any inhibition of BCRP in the liver or kidney or induction of CYP3A4 enzyme in the liver.

Therefore, the dosage of macitentan may be 60 to 90 mg per day in aspect (n). Preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. A further preferred dosage range is 72 to 78 mg per day.

Further, the dosage of macitentan may be escalated from 10 mg per day, followed by 25 to 50 mg per day, preferably 37.5 mg per day, followed by 60 to 90 mg per day, preferably 75 mg per day, optionally followed by 100 to 200 mg per day, preferably 150 mg per day.

In a preferred aspect, these combinations relate to macitentan for use in the treatment and/or prevention of mild or moderate PAH, preferably moderate PAH.

(o) A further aspect of the present invention relates to macitentan for use in the treatment and/or prevention of PAH according to aspect (n), wherein the PDE5 inhibitor is selected from sildenafil, tadalafil, vardenafil, and udenafil; the prostacyclin analogue is selected from epoprostenol, treprostinil, iloprost, and beraprost; the prostacyclin receptor agonist is selected from selexipag and ralinepag; and the soluble guanylate cyclase stimulator is selected from riociguat and vericiguat.

Therein, macitentan has a dosage or dosage regimen according to any one of aspects (a) to (l) and (n). In a preferred aspect, these dosages relate to macitentan for use in the treatment and/or prevention of mild or moderate PAH.

In a preferred aspect, these combinations relate to macitentan for use in the treatment and/or prevention of mild or moderate PAH, preferably moderate PAH.

(p) A further aspect of the present invention relates to macitentan for use in the treatment and/or prevention of PAH according to aspect (n) or (o), wherein macitentan is combined with tadalafil and/or selexipag or ralinepag. Preferably, macitentan is combined with tadalafil and/or selexipag.

Therein, macitentan has a dosage or dosage regimen according to any one of aspects (a) to (k) and (n). In a preferred aspect, these dosages relate to macitentan for use in the treatment and/or prevention of mild or moderate PAH.

In a preferred aspect, these combinations relate to macitentan for use in the treatment and/or prevention of mild or moderate PAH, preferably moderate PAH.

(q) A further aspect of the present invention relates to macitentan for use in the treatment and/or prevention of PAH according to aspect (p), wherein tadalafil, if applicable, has a dose of 20 to 40 mg per day, preferably 40 mg per day, selexipag, if applicable, has a dose of 0.2 to 1.6 mg twice per day, and ralinepag, if applicable, has a dose of 0.05 to 1.45 mg per day.

Therein, macitentan has a dosage or dosage regimen according to any one of aspects (a) to (k) and (n). In a preferred aspect, these dosages relate to macitentan for use in the treatment and/or prevention of mild or moderate PAH.

In a preferred aspect, these combinations relate to macitentan for use in the treatment and/or prevention of mild or moderate PAH, preferably moderate PAH.

(r) A further aspect of the present invention relates to a pharmaceutical composition for use in the treatment of PAH comprising macitentan and at least a pharmaceutically acceptable excipient, containing macitentan in an amount of more than 20 mg to equal to or less than 300 mg, for example, more than 20 mg to less than 250 mg, preferably 37.5 mg, 75 mg or 150 mg, more preferably 37.5 mg or 75 mg, most preferably 75 mg.

It is to be understood that macitentan may have a dosage according to any one of the daily dosages of aspects (a) to (e).

In a preferred aspect, the pharmaceutical composition is for use in the treatment and/or prevention of mild or moderate PAH.

(s) A further aspect of the present invention relates to the pharmaceutical composition according to aspect (r), which comprises
    i) macitentan in a total amount of 10 to 50% in weight based on the total weight of the pharmaceutical composition,
    ii) a filler, consisting of lactose monohydrate with microcrystalline cellulose, in a total amount of 10 to 85% in weight based on the total weight of the pharmaceutical composition,
    iii) a disintegrant, consisting of sodium starch glycolate or a combination of sodium starch glycolate and polyvinylpyrrolidone, in a total amount of 1 to 10% in weight based on the total weight of the pharmaceutical composition,
    iv) a surfactant, consisting of a polysorbate, in a total amount of 0.1 to 1% in weight based on the total weight of the pharmaceutical composition, and
    v) a lubricant, consisting of magnesium stearate, in a total amount of 0.05 to 5% in weight based on the total weight of the pharmaceutical composition.

(t) A further aspect of the present invention relates to the pharmaceutical composition according to aspect (r) or (s), which is in the form of a capsule or a tablet (in particular in the form of a tablet, notably a tablet containing 75 mg of macitentan).

(u) A further aspect of the present invention relates to macitentan for use in the treatment and/or prevention of PAH according to any one of aspects (a) to (q), wherein the treatment and/or prevention means the reduction of morbidity and/or mortality risk of PAH. That is, this aspect of the present invention relates to macitentan for use in reducing morbidity and/or mortality risk of PAH, in which macitentan is used in a manner according to any one of aspects (a) to (q).

The reduction of morbidity and/or mortality risk of PAH may be evaluated as the reduction of the composite morbidity/mortality risk, for example, by time to first clinical worsening up to 7 days after EOT (End of Treatment), defined as time from baseline to the first of the following events (the primary endpoint):
    Death (all-cause mortality);
    Pulmonary hypertension related hospitalization (including for worsening of PAH, atrial septostomy, lung transplantation with or without heart transplantation, or initiation of parenteral prostacyclins);
    Worsening of PAH resulting in initiation of parenteral prostanoid therapy;
    Pulmonary hypertension related disease progression, defined as:
        For functional class II and III patients at baseline (both criteria have to be satisfied):
            More than 15% decrease in 6-minute walk distance (6MWD) from baseline, confirmed by two 6MWD tests performed on separate days within 2 weeks of each other;
            Initiation of additional PAH therapy or Worsening of WHO Functional Class;
        For functional class IV patients at baseline (both criteria have to be satisfied):
            More than 15% decrease in 6MWD from baseline, confirmed by two 6MWD tests performed on separate days within 2 weeks of each other;
            Initiation of additional PAH therapy.

Alternatively, the reduction of morbidity and/or mortality risk of PAH may be evaluated separately.

The above evaluation may be made for example by the following schedule:
    i) Run-in period (for example 4 weeks) with the dosage of macitentan of 10 mg per day;
    ii) Titration period (for example 4 weeks) with the dosage of macitentan of 37.5 mg per day;
    iii) Maintenance period with the dosage of macitentan of 75 mg per day.

The above evaluation may be made for example by a double blind test with the control group receiving the dosage of macitentan of 10 mg per day in the titration and maintenance period.

For reducing the morbidity and/or mortality risk of PAH, the dosage of macitentan may be 60 to 90 mg per day. Preferably, the dosage is 65 to 85 mg per day, more preferably the dosage is 70 to 80 mg per day and most preferably the dosage is 75 mg per day. It is to be understood that each of the lower limits disclosed above may be combined with each of the upper limits, i.e. the dosage could also be from 60 to 85 mg, from 60 to 80 mg, or from 60 to 75 mg per day. Also disclosed are dosages from 65 to 90 mg, or 65 to 75 mg per day. A further preferred dosage range is 72 to 78 mg per day.

Further, the dosage of macitentan may be escalated from 10 mg per day, followed by 25 to 50 mg per day, preferably 37.5 mg per day, followed by 60 to 90 mg per day, preferably 75 mg per day, optionally followed by 100 to 200 mg per day, preferably 150 mg per day.

It is to be understood that all disclosed aspects are to be regarded as disclosed also in the form of macitentan for the manufacture of a medicament for the uses according to any one of aspects (a) to (q) and (u):

(a') One aspect of the present invention relates to macitentan for the manufacture of a medicament for use in the treatment and/or prevention of pulmonary arterial hypertension (PAH) in human, wherein the dosage of macitentan is more than 20 mg per day to equal to or less than 300 mg per day, for example, more than 20 mg per day to less than 250 mg per day. It is to be understood that the disclosure of aspect (a) applies analogously.

(b') Another aspect of the present invention relates to macitentan for the manufacture of a medicament for use in the treatment and/or prevention of pulmonary arterial hypertension (PAH) according to aspect (a'), wherein the PAH is mild or moderate PAH, preferably moderate PAH. It is to be understood that the disclosure of aspect (b) applies analogously.

(c') Another aspect of the present invention relates to macitentan for the manufacture of a medicament for use in the treatment and/or prevention of PAH according to aspect (a') or (b'), wherein the dosage of macitentan is 60 to 90 mg per day, preferably 65 to 85 mg per day, more preferably 70 to 80 mg per day and most preferably 75 mg per day. It is to be understood that the disclosure of aspect (c) applies analogously.

(d') Another aspect of the present invention relates to macitentan for the manufacture of a medicament for use in the treatment and/or prevention of PAH according to aspect (a') or (b'), wherein the dosage of macitentan is 25 to 50 mg per day, preferably 30 to 45 mg per day, more preferably 35 to 40 mg per day and most preferably 37.5 mg per day. It is to be understood that the disclosure of aspect (d) applies analogously.

(e') Another aspect of the present invention relates to macitentan for the manufacture of a medicament for use in the treatment and/or prevention of PAH according to aspect (a') or (b'), wherein the dosage of macitentan is 110 to 200 mg per day, preferably 125 to 175 mg per day, more preferably 140 to 160 mg per day and most preferably 150 mg per day. It is to be understood that the disclosure of aspect (e) applies analogously.

(f') Another aspect of the present invention relates to macitentan for the manufacture of a medicament for use in the treatment and/or prevention of PAH according to aspect (a') or (b'), wherein the dosage of macitentan is 60 to 90 mg twice per day, preferably 65 to 85 mg twice per day, more preferably 70 to 80 mg twice per day and most preferably 75 mg twice per day. It is to be understood that the disclosure of aspect (f) applies analogously.

(g') Another aspect of the present invention relates to macitentan for the manufacture of a medicament for use in the treatment and/or prevention of PAH according to aspect (a') or (b'), wherein the dosage of macitentan is 25 to 50 mg twice per day, preferably 30 to 45 mg twice per day, more preferably 35 to 40 mg twice per day and most preferably 37.5 mg twice per day. It is to be understood that the disclosure of aspect (g) applies analogously.

(h') Another aspect of the present invention relates to macitentan for the manufacture of a medicament for use in the treatment and/or prevention of PAH according to aspect (a') or (b'), wherein the dosage of macitentan is escalated from 10 mg per day, followed by 25 to 50 mg per day, preferably 37.5 mg per day, and optionally followed by 60 to 90 mg per day, preferably 75 mg per day. It is to be understood that the disclosure of aspect (h) applies analogously.

(i') Another aspect of the present invention relates to macitentan for the manufacture of a medicament for use in the treatment and/or prevention of PAH according to aspect (a) or (b), wherein the dosage of macitentan is escalated from 10 mg per day, followed by 60 to 90 mg per day, preferably 75 mg once per day or 37.5 mg twice a day. It is to be understood that the disclosure of aspect (i) applies analogously.

(j') Another aspect of the present invention relates to macitentan for the manufacture of a medicament for use in the treatment and/or prevention of PAH according to aspect (h'), wherein the dosage of macitentan is escalated from 10 mg once per day, preferably for 15 to 45 days; followed by 25 to 50 mg per day, preferably 37.5 mg once per day, preferably for 15 to 45 days; and optionally followed by 60 to 90 mg per day, preferably by 75 mg once per day or 37.5 mg twice per day. It is to be understood that the disclosure of aspect (j) applies analogously.

(k') Another aspect of the present invention relates to macitentan for the manufacture of a medicament for use in the treatment and/or prevention of PAH according to aspect (i'), wherein the dosage of macitentan is escalated from 10 mg once per day, preferably for 15 to 45 days; followed by 60 to 90 mg per day, preferably by 75 mg once per day or 37.5 mg twice per day. It is to be understood that the disclosure of aspect (k) applies analogously.

(l') Another aspect of the present invention relates to macitentan for the manufacture of a medicament for use in the treatment and/or prevention of PAH according to any one of aspects (a') to (d'), wherein the dosage of macitentan is escalated from 25 to 50 mg per day, preferably 37.5 mg per day, preferably for 15 to 45 days; optionally followed by 60 to 90 mg per day, preferably by 75 mg per day; provided that the patient is already treated with an endothelin receptor antagonist preferably selected from bosentan and ambrisentan. It is to be understood that the disclosure of aspect (l) applies analogously.

(m') Another aspect of the present invention relates to macitentan for the manufacture of a medicament for use in the treatment and/or prevention of PAH according to any one of aspects (a') to (c'), wherein the dosage of macitentan is 60 to 90 mg per day, preferably 75 mg per day; provided that the patient is already treated with an endothelin receptor antagonist preferably selected from bosentan and ambrisentan. It is to be understood that the disclosure of aspect (m) applies analogously.

(n') Another aspect of the present invention relates to macitentan for the manufacture of a medicament for use in the treatment and/or prevention of PAH according to any one of aspects (a') to (m'), wherein macitentan is combined with a PDE5 inhibitor and/or a prostacyclin analogue, and/or a prostacyclin receptor agonist and/or a soluble guanylate cyclase stimulator. It is to be understood that the disclosure of aspect (n) applies analogously.

(o') Another aspect of the present invention relates to macitentan for the manufacture of a medicament for use in the treatment and/or prevention of PAH according to aspect (n'), wherein the PDE5 inhibitor is selected from sildenafil, tadalafil, vardenafil, and udenafil; the prostacyclin analogue is selected from epoprostenol, treprostinil, iloprost, and beraprost; the prostacyclin receptor agonist is selected from selexipag and ralinepag; and the soluble guanylate cyclase stimulator is selected from riociguat and vericiguat. It is to be understood that the disclosure of aspect (o) applies analogously.

(p') Another aspect of the present invention relates to macitentan for the manufacture of a medicament for use in the treatment and/or prevention of PAH according to aspect (n) or (o'), wherein macitentan is combined with tadalafil and/or selexipag or ralinepag, preferably tadalafil and/or selexipag. It is to be understood that the disclosure of aspect (p) applies analogously.

(q') Another aspect of the present invention relates to macitentan for the manufacture of a medicament for use in the treatment and/or prevention of PAH according to aspect (p'), wherein tadalafil, if applicable, has a dose of 20 to 40 mg per day, preferably 40 mg per day, selexipag, if applicable, has a dose of 0.2 to 1.6 mg twice per day and ralinepag, if applicable, has a dose of 0.05 to 1.45 mg per day. It is to be understood that the disclosure of aspect (q) applies analogously.

(u') Another aspect of the present invention relates to macitentan for the manufacture of a medicament for use in the treatment and/or prevention of PAH according to any one of aspects (a') to (q'), wherein the treatment and/or prevention means the reduction of morbidity and/or mortality risk of PAH. That is, this aspect of the present invention relates to macitentan for the manufacture of a medicament in reducing morbidity and/or mortality risk of PAH, in which macitentan is administered in a manner according to any one of aspects (a') to (q'). It is to be understood that the disclosure of aspect (u) applies analogously.

It is to be understood that the comments and details of aspects (a) to (q) and (u) also apply to aspects (a') to (q') and (u').

Moreover, it is to be understood that all disclosed aspects (a) to (q) and (u) are to be regarded as disclosed also in the form of a method of treatment:

(a") One aspect of the present invention relates to a method of treatment and/or prevention of pulmonary arterial hypertension (PAH) in human, said method comprising administering macitentan in a dosage of more than 20 mg per day to equal to or less than 300 mg per day, for example, more than 20 mg per day to less than 250 mg per day to a subject in need thereof. It is to be understood that the disclosure of aspect (a) applies analogously.

(b") Another aspect of the present invention relates to a method of treatment and/or prevention of pulmonary arterial hypertension (PAH) according to aspect (a"), wherein the PAH is mild or moderate PAH, preferably moderate PAH. It is to be understood that the disclosure of aspect (b) applies analogously.

(c") Another aspect of the present invention relates to a method of treatment and/or prevention of pulmonary arterial hypertension (PAH) according to aspect (a") or (b"), wherein the dosage of macitentan is 60 to 90 mg per day, preferably 65 to 85 mg per day, more preferably 70 to 80 mg per day and most preferably 75 mg per day. It is to be understood that the disclosure of aspect (c) applies analogously.

(d") Another aspect of the present invention relates to a method of treatment and/or prevention of pulmonary arterial hypertension (PAH) according to aspect (a") or (b"), wherein the dosage of macitentan is 25 to 50 mg per day, preferably 30 to 45 mg per day, more preferably 35 to 40 mg per day and most preferably 37.5 mg per day. It is to be understood that the disclosure of aspect (d) applies analogously.

(e") Another aspect of the present invention relates to a method of treatment and/or prevention of pulmonary arterial hypertension (PAH) according to aspect (a") or (b"), wherein the dosage of macitentan is 110 to 200 mg per day, preferably 125 to 175 mg per day, more preferably 140 to 160 mg per day and most preferably 150 mg per day. It is to be understood that the disclosure of aspect (e) applies analogously.

(f") Another aspect of the present invention relates to a method of treatment and/or prevention of pulmonary arterial hypertension (PAH) according to aspect (a") or (b"), wherein the dosage of macitentan is 60 to 90 mg twice per day, preferably 65 to 85 mg twice per day, more preferably 70 to 80 mg twice per day and most preferably 75 mg twice per day. It is to be understood that the disclosure of aspect (f) applies analogously.

(g") Another aspect of the present invention relates to a method of treatment and/or prevention of pulmonary arterial hypertension (PAH) according to aspect (a") or (b"), wherein the dosage of macitentan is 25 to 50 mg twice per day, preferably 30 to 45 mg twice per day, more preferably 35 to 40 mg twice per day and most preferably 37.5 mg twice per day. It is to be understood that the disclosure of aspect (g) applies analogously.

(h") Another aspect of the present invention relates to a method of treatment and/or prevention of pulmonary arterial hypertension (PAH) according to aspect (a") or (b"), wherein the dosage of macitentan is escalated from 10 mg per day, followed by 25 to 50 mg per day, preferably 37.5 mg per day, and optionally followed by 60 to 90 mg per day, preferably 75 mg per day. It is to be understood that the disclosure of aspect (h) applies analogously.

(i") Another aspect of the present invention relates to a method of treatment and/or prevention of pulmonary arterial hypertension (PAH) according to aspect (a") or (b"), wherein the dosage of macitentan is escalated from 10 mg per day, followed by 60 to 90 mg per day, preferably 75 mg once per day or 37.5 mg twice a day. It is to be understood that the disclosure of aspect (i) applies analogously.

(j") Another aspect of the present invention relates to a method of treatment and/or prevention of pulmonary arterial hypertension (PAH) according to aspect (h"), wherein the dosage of macitentan is escalated from 10 mg once per day, preferably for 15 to 45 days; followed by 25 to 50 mg per day, preferably 37.5 mg once per day, preferably for 15 to 45 days; and optionally followed by 60 to 90 mg per day, preferably by 75 mg once per day or 37.5 mg twice per day. It is to be understood that the disclosure of aspect (j) applies analogously.

(k") Another aspect of the present invention relates to a method of treatment and/or prevention of pulmonary arterial hypertension (PAH) according to aspect (i"), wherein the dosage of macitentan is escalated from 10 mg once per day, preferably for 15 to 45 days; followed by 60 to 90 mg per day, preferably by 75 mg once per day or 37.5 mg twice per day. It is to be understood that the disclosure of aspect (k) applies analogously.

(l") Another aspect of the present invention relates to a method of treatment and/or prevention of pulmonary arterial hypertension (PAH) according to any one of aspects (a") to (d"), wherein the dosage of macitentan is escalated from 25 to 50 mg per day, preferably 37.5 mg per day, preferably for 15 to 45 days; optionally followed by 60 to 90 mg per day, preferably by 75 mg per day; provided that the patient is already treated with an endothelin receptor antagonist preferably selected from bosentan and ambrisentan. It is to be understood that the disclosure of aspect (l) applies analogously.

(m") Another aspect of the present invention relates to a method of treatment and/or prevention of pulmonary arterial hypertension (PAH) according to any one of aspects (a") to (c"), wherein the dosage of macitentan is 60 to 90 mg per day, preferably 75 mg per day; provided that the patient is already treated with an endothelin receptor antagonist preferably selected from bosentan and ambrisentan. It is to be understood that the disclosure of aspect (m) applies analogously.

(n") Another aspect of the present invention relates to a method of treatment and/or prevention of pulmonary arterial hypertension (PAH) according to any one of aspects (a") to (m"), wherein macitentan is combined with a PDE5 inhibitor and/or a prostacyclin analogue, and/or a prostacyclin receptor agonist and/or a soluble guanylate cyclase stimulator. It is to be understood that the disclosure of aspect (n) applies analogously.

(o") Another aspect of the present invention relates to a method of treatment and/or prevention of pulmonary arterial hypertension (PAH) according to aspect (n"), wherein the PDE5 inhibitor is selected from sildenafil, tadalafil, vardenafil, and udenafil; the prostacyclin analogue is selected from epoprostenol, treprostinil, iloprost, and beraprost; the prostacyclin receptor agonist is selected from selexipag and ralinepag; and the soluble guanylate cyclase stimulator is selected from riociguat and vericiguat. It is to be understood that the disclosure of aspect (o) applies analogously.

(p") Another aspect of the present invention relates to a method of treatment and/or prevention of pulmonary arterial hypertension (PAH) according to aspect (n") or (o"), wherein macitentan is combined with tadalafil and/or selexipag or ralinepag, preferably tadalafil and/or selexipag. It is to be understood that the disclosure of aspect (p) applies analogously.

(q") Another aspect of the present invention relates to a method of treatment and/or prevention of pulmonary arterial hypertension (PAH) according to aspect (p"), wherein tadalafil, if applicable, has a dose of 20 to 40 mg per day, preferably 40 mg per day, selexipag, if applicable, has a dose of 0.2 to 1.6 mg twice per day and ralinepag, if applicable, has a dose of 0.05 to 1.45 mg per day. It is to be understood that the disclosure of aspect (q) applies analogously.

(u") Another aspect of the present invention relates to a method of treatment and/or prevention of PAH according to any one of aspects (a") to (q"), wherein the treatment and/or prevention means the reduction of morbidity and/or mortality risk of PAH. That is, this aspect of the present invention relates to a method of reducing morbidity and/or mortality risk of PAH, in which macitentan is administered in a manner according to any one of aspects (a") to (q"). It is to be understood that the disclosure of aspect (u) applies analogously.

It is to be understood that the comments and details of aspects (a) to (q) also apply to aspects (a") to (q") and (u").

According to a further aspect of the present invention, in each of the above-mentioned aspects, that is, in each of aspects (a) to (t) and (u), (a') to (q') and (u') as well as (a") to (q") and (u"), macitentan can be replaced by its active metabolite, known under the code name ACT-132577 and the International Non-proprietary Name aprocitentan, which has the chemical formula

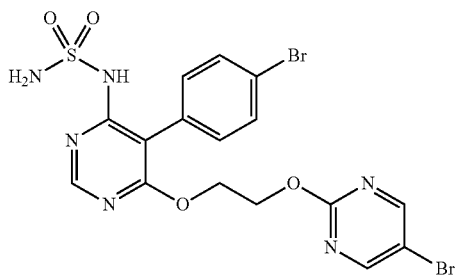 [SMILES: NS(=O)(=O)Nc1ncnc(OCCOc2ncc(Br)cn2)c1-c1ccc(Br)cc1]

whereby any weight amount of macitentan will be replaced a 5-fold weight amount of aprocitentan.

For example, taking aspect (c) of the invention described above, a further aspect of the invention relates to aprocitentan for use in the treatment and/or prevention of PAH according to aspect (a) or (b) wherein the weight amounts of macitentan aprocitentan will be replaced a 5-fold weight amount of aprocitentan, wherein the dosage of aprocitentan is 300 to 450 mg per day. Preferably, the dosage of aprocitentan is 325 to 425 mg per day, more preferably the dosage of aprocitentan is 350 to 400 mg per day and most preferably the dosage of aprocitentan is 375 mg per day. It is to be understood that each of the lower limits disclosed above may be combined with each of the upper limits, i.e. the dosage of aprocitentan could also be from 300 to 425 mg, from 300 to 400 mg, or from 300 to 375 mg per day. Also disclosed are dosages of aprocitentan from 325 to 450 mg, or 325 to 375 mg per day. Further preferred ranges are 360 to 390 mg of aprocitentan per day. According to a more preferred aspect, these dosages of aprocitentan are applied once a day. In a preferred aspect, these dosages relate to aprocitentan for use in the treatment and/or prevention of mild or moderate PAH, preferably moderate PAH.

Moreover, the following abbreviations are used throughout the present specification.

Abbreviations

APAH-CTD PAH associated with connective tissue disease
APAH-PoPH PAH associated with porto-pulmonary hypertension
aq. aqueous
BNP brain natriuretic peptide
BPM beats per minute
CI cardiac index
DLCO diffusing capacity of lung for CO (carbon monoxide)
EDTA ethylenediaminetetraacetic acid
ERA endothelin receptor antagonist
ET endothelin
FPAH familial PAH
HR heart rate
IgG immunoglobulin G
$K_2$EDTA ethylenediaminetetraacetic acid dipotassium salt
mPAP mean pulmonary artery pressure
6MWD 6-minute walk distance
NT-proBNP N-terminal pro-brain natriuretic peptide
PAH pulmonary arterial hypertension
PAOP pulmonary artery occlusion pressure, which is synonymous with PAWP
PAWP pulmonary capillary wedge pressure, which is synonymous with PAOP
PAP pulmonary artery pressure
PBS phosphate buffered saline
PD pharmacodynamics
PDE5 cyclic guanosine 3',5'-monophosphate (cGMP) phosphodiesterase type 5
PDE5 is PDE5 inhibitors
PH pulmonary hypertension
PK pharmacokinetics
PVR pulmonary vascular resistance
RAP right arterial pressure (sometimes also referred to as mRAP)
RHC right heart catheterization
SBP systolic systemic blood pressure
$SvO_2$ mixed venous oxygen saturation
Tris tris(hydroxymethyl)aminomethane
WHO World Health Organization
WHO FC World Health Organization Functional Class

EXPERIMENTAL PART

The following non-limitative examples illustrate the invention.

EXAMPLES

Effect of Macitentan on Decrease in Hemoglobin Concentration

Hemoglobin measurements were pooled from 3 Phase I clinical studies in healthy volunteers:

Study AC-055-102: Investigation of the PK, PD, safety and tolerability of macitentan in male subjects (the study protocol is described in the following publication: Sidharta et al., Safety, tolerability, pharmacokinetics, and pharmacodynamics of macitentan, an endothelin receptor antagonist, in an ascending multiple-dose study in healthy subjects. *J. Clin. Pharmacol.* (2013), 53(11), 1131-1138)

Study AC-055-116: Investigation of the PK, PD, safety and tolerability of macitentan in male Japanese subjects (the study protocol is described in the following publication: Yokoyama et al., Tolerability, Safety, Pharmacokinetics, and Pharmacodynamics of Macitentan, a New Endothelin Receptor Antagonist, in Healthy Japanese Male Subjects. *Rinsho yakuri/Japanese Journal of Clinical Pharmacology and Therapeutics* (2016), 47, 143-150)

Study AC-055-117: Investigation of the PK, PD, safety and tolerability of macitentan in male Korean subjects (the study protocol is described in the following publication: Ahn et al., Pharmacokinetic-pharmacodynamic relationships of macitentan, a new endothelin receptor antagonist, after multiple dosing in healthy Korean subjects, *Am. J. Cardiovasc. Drugs* (2014), 14(5), 377-385)

Hemoglobin concentrations measured in the morning of Day 11 of macitentan treatment and at baseline on Day −1 were used in the analysis. Changes in hemoglobin concentrations compared to baseline were regressed against the different dose levels of macitentan, including placebo.

An Emax curve with baseline was fitted and the following parameters were estimated by nonlinear regression:

E0: Change in hemoglobin without macitentan

Emax: Maximum change in hemoglobin theoretically could be elicited by macitentan ED50: the dose resulting in 50% reduction of hemoglobin The following formula was used:

$$\text{Change in hemoglobin} = E0 + ((\text{Macitentan dose} \times E_{max})/(\text{Macitentan dose} + ED50))$$

The resulting dose-response curve is shown in FIG. 1.

Based on the analysis, the maximum effect of macitentan on hemoglobin decrease would be around 1.23 g/dL and the effect of macitentan on hemoglobin decrease plateaus already at the 10 mg dose (see FIG. 1). Therefore, no clinically relevant decrease in hemoglobin is expected above a 10 mg dose of macitentan in humans.

What is claimed is:

1. A method of administering macitentan to a human patient having pulmonary arterial hypertension (PAH), comprising
    administering the macitentan to the patient at a dosage of 10 mg per day for a first period of time that is 15 to 45 days; followed by
    administering the macitentan to the patient at a dosage of 25 mg to 50 mg per day for a second period of time that is 15 to 45 days; and followed by
    administering the macitentan to the patient at a dosage of 60 mg to 90 mg per day for a maintenance period of time.

2. The method of claim 1, wherein the first period of time is 15 days.

3. The method of claim 2, wherein the second period of time is 15 days.

4. The method of claim 1, wherein the macitentan is administered at a dosage of 70 mg to 80 mg per day for the maintenance period of time.

5. The method of claim 4, wherein the macitentan is administered at a dosage of 35 mg to 40 mg per day for the second period of time.

6. The method of claim 3, wherein the macitentan is administered at a dosage of 70 mg to 80 mg per day for the maintenance period of time.

7. The method of claim 6, wherein the macitentan is administered at a dosage of 35 mg to 40 mg per day for the second period of time.

8. The method of claim 1, wherein the macitentan is administered at a dosage of 75 mg per day for the maintenance period of time.

9. The method of claim 8, wherein the macitentan is administered at a dosage of 37.5 mg twice per day for the maintenance period of time.

10. The method of claim 8, wherein the macitentan is administered at a dosage of 37.5 mg per day for the second period of time.

11. The method of claim 3, wherein the macitentan is administered at a dosage of 75 mg per day for the maintenance period of time.

12. The method of claim 11, wherein the macitentan is administered at a dosage of 37.5 mg twice per day for the maintenance period of time.

13. The method of claim 11, wherein the macitentan is administered at a dosage of 37.5 mg per day for the second period of time.

14. The method of claim 1, wherein the method reduces a morbidity risk, a mortality risk, or both, of the PAH.

15. The method of claim 1, wherein the PAH is mild or moderate PAH.

16. The method of claim 15, wherein the PAH is moderate PAH.

17. The method of claim 1, further comprising administering to the patient a PDE5 inhibitor, a prostacyclin analogue, a prostacyclin receptor agonist, or a soluble guanylate cyclase stimulator, or a combination thereof.

18. The method of claim 17, wherein the PDE5 inhibitor is sildenafil, tadalafil, vardenafil, or udenafil; the prostacyclin analogue is epoprostenol, treprostinil, iloprost, or beraprost; the prostacyclin receptor agonist is selexipag or ralinepag; and the soluble guanylate cyclase stimulator is riociguat or vericiguat.

19. The method of claim 1, further comprising administering to the patient tadalafil, selexipag, or ralinepag, or a combination thereof.

20. The method of claim 19, wherein the tadalafil is administered in a dose of 20 to 40 mg per day, the selexipag is administered in a dose of 0.2 to 1.6 mg twice per day, and ralinepag is administered in a dose of 0.05 mg to 1.45 mg per day.

21. The method of claim 20, wherein the dose of tadalafil is 40 mg per day.

22. The method of claim 1, further comprising administering to the patient tadalafil or selexipag, or combinations thereof.

23. The method of claim 1, wherein the second period of time is 28 to 30 days.

24. The method of claim 23, wherein the first period of time is 28 to 30 days.

25. The method of claim 23, wherein the macitentan is administered at a dosage of 70 mg to 80 mg per day for the maintenance period of time.

26. The method of claim 25, wherein the macitentan is administered at a dosage of 35 mg to 40 mg per day for the second period of time.

27. The method of claim 23, wherein the macitentan is administered at a dosage of 75 mg per day for the maintenance period of time.

28. The method of claim 27, wherein the macitentan is administered at a dosage of 37.5 mg per day for the second period of time.

29. The method of claim 24, wherein the macitentan is administered at a dosage of 75 mg per day for the maintenance period of time.

30. The method of claim 29, wherein the macitentan is administered at a dosage of 37.5 mg per day for the second period of time.

\* \* \* \* \*